(12) United States Patent
Erickson et al.

(10) Patent No.: US 8,434,616 B2
(45) Date of Patent: May 7, 2013

(54) SHARPS CONTAINER

(75) Inventors: Thomas E. Erickson, Crosslake, MN (US); James J. Erickson, Mound, MN (US); Thomas Sauro, Rosemount, MN (US)

(73) Assignee: Ultimed, Inc., St. Paul, MN (US)

( * ) Notice: Subject to any disclaimer, the term of this patent is extended or adjusted under 35 U.S.C. 154(b) by 102 days.

(21) Appl. No.: 12/247,698

(22) Filed: Oct. 8, 2008

(65) Prior Publication Data

US 2010/0084293 A1 Apr. 8, 2010

(51) Int. Cl.
*B65D 83/10* (2006.01)

(52) U.S. Cl.
USPC .................................. 206/366; 220/908

(58) Field of Classification Search .............. 206/366, 206/370, 363, 438, 497, 216, 223, 577, 585; 220/4.21, 908
See application file for complete search history.

(56) References Cited

U.S. PATENT DOCUMENTS

| | | | | |
|---|---|---|---|---|
| 4,576,281 A | * | 3/1986 | Kirksey | 206/370 |
| 4,662,516 A | * | 5/1987 | Baker et al. | 206/363 |
| 4,709,817 A | * | 12/1987 | Keady et al. | 206/523 |
| 4,722,472 A | | 2/1988 | Bruno | |
| 4,750,619 A | * | 6/1988 | Cohen et al. | 206/438 |
| 4,862,573 A | | 9/1989 | Kelson | |
| 4,890,733 A | | 1/1990 | Anderson | |
| 4,927,073 A | | 5/1990 | Esposito | |
| 4,978,028 A | * | 12/1990 | George et al. | 229/117.28 |
| 5,046,614 A | | 9/1991 | Torres | |
| 5,065,939 A | * | 11/1991 | Boothe et al. | 229/151 |
| 5,097,950 A | | 3/1992 | Weiss | |
| 5,127,522 A | | 7/1992 | Ranford | |
| 5,152,394 A | | 10/1992 | Hughes | |
| 5,190,185 A | | 3/1993 | Blechl | |
| 5,205,409 A | * | 4/1993 | Bruno | 206/370 |
| 5,222,599 A | * | 6/1993 | Boyce | 206/366 |
| 5,240,108 A | * | 8/1993 | Tonna | 206/366 |
| 5,394,982 A | | 3/1995 | Sawaya | |
| 5,409,113 A | * | 4/1995 | Richardson et al. | 206/366 |
| 5,413,243 A | | 5/1995 | Bemis et al. | |
| 5,494,158 A | * | 2/1996 | Erickson | 206/366 |
| 5,573,113 A | | 11/1996 | Shillington et al. | |
| 5,603,404 A | * | 2/1997 | Nazare et al. | 206/366 |
| 5,630,506 A | | 5/1997 | Thorne et al. | |
| 5,833,057 A | * | 11/1998 | Char et al. | 206/204 |
| 5,848,692 A | * | 12/1998 | Thorne et al. | 206/366 |
| 5,975,349 A | * | 11/1999 | Menes | 221/232 |
| 6,283,909 B1 | | 9/2001 | Sharp | |
| 6,474,472 B1 | * | 11/2002 | Shaw | 206/366 |
| 6,685,017 B2 | | 2/2004 | Erickson | |
| 6,745,898 B2 | | 6/2004 | Lin | |
| 6,923,318 B1 | * | 8/2005 | Erickson et al. | 206/366 |
| 6,923,319 B1 | | 8/2005 | Erickson | |

(Continued)

FOREIGN PATENT DOCUMENTS

WO 94/24021 A1 10/1994

*Primary Examiner* — Mickey Yu
*Assistant Examiner* — Rafael Ortiz
(74) *Attorney, Agent, or Firm* — Seager, Tufte & Wickhem LLC (57) ABSTRACT

The disclosure relates to volumetrically efficient systems for distributing, storing, and dispensing a number of medical or laboratory sharps with subsequent safe disposal of the used sharps. The systems comprise first and second sharps containers configured such that the combined containers, as well as contained sharps, may be shipped in a volume approximately equivalent to the volume of one of the containers.

14 Claims, 5 Drawing Sheets

U.S. PATENT DOCUMENTS

| | | | |
|---|---|---|---|
| 7,344,027 B2 | 3/2008 | Erickson | |
| 7,383,953 B2 * | 6/2008 | Dickinson | 206/522 |
| 7,513,363 B2 * | 4/2009 | Brown et al. | 206/366 |
| 7,516,844 B2 * | 4/2009 | Erickson et al. | 206/366 |
| 7,556,149 B2 * | 7/2009 | Erickson et al. | 206/366 |
| 7,562,025 B2 * | 7/2009 | Mallett et al. | 705/1.1 |
| 7,815,046 B2 * | 10/2010 | Sansoucy et al. | 206/366 |
| 2003/0040715 A1 | 2/2003 | D'Antonio | |
| 2003/0213714 A1 * | 11/2003 | Moats et al. | 206/366 |
| 2005/0103662 A1 * | 5/2005 | Iske et al. | 206/366 |
| 2005/0258058 A1 * | 11/2005 | Panek et al. | 206/364 |
| 2005/0269227 A1 * | 12/2005 | Erickson et al. | 206/366 |
| 2005/0269320 A1 * | 12/2005 | Erickson et al. | 220/4.21 |
| 2006/0032769 A1 | 2/2006 | Erickson | |
| 2006/0243618 A1 * | 11/2006 | Brown et al. | 206/366 |
| 2006/0243619 A1 * | 11/2006 | Brown et al. | 206/366 |
| 2006/0243635 A1 * | 11/2006 | Sullivan et al. | 206/571 |
| 2008/0067100 A1 * | 3/2008 | Japuntich et al. | 206/571 |
| 2008/0135434 A1 | 6/2008 | Erickson | |
| 2009/0120820 A1 * | 5/2009 | Iske et al. | 206/366 |
| 2009/0120821 A1 * | 5/2009 | Japuntich et al. | 206/366 |
| 2009/0236347 A1 * | 9/2009 | Erickson et al. | 220/529 |

* cited by examiner

SHARPS CONTAINER

BACKGROUND OF THE INVENTION

A world-wide health care problem and need is the disposal of used syringes; this is a continuing health threat to the public. Of great concern, of course, are AIDS and other serious infectious diseases such as hepatitis. And, needles can become contaminated when used to treat various conditions such as allergies, infertility, arthritis, migraines, HIV, growth hormones among others.

Health care regulations have mandated the safe disposal of used syringes. A number of approaches, procedures and apparatus have been proposed for the storage of used syringes and the subsequent disposal thereof.

After a needle has been used either by or on a patient, then the syringe needle is contaminated from contact with the blood of the patient. If the user is HIV positive or a carrier of hepatitis or other blood born pathogen, then an accidental needle stick by the contaminated needle could spread the disease.

In hospitals and clinics the health care industry uses special containers dedicated for the disposal of needles and other invasive devices. Such containers are frequently referred to as "sharps" containers. The sharps containers with used syringes/needles therein are then disposed by industrial waste collectors and are usually either burned, disintegrated or buried, depending upon local health care regulations.

There is an additional dimension to the problem; that is the uses of syringes in private homes. For example, home syringe users are frequently diabetics who require frequent doses of insulin to regulate their glucose level. The practice of disposing and safe storage of used syringe syringes in private homes is far less organized than in hospitals and clinics. Home disposing techniques are varied and frequently home invented, using discarded or empty containers found around the home; such arrangements are high risk for accidental spreading of disease. There is currently no standard disposal practice for insulin users.

Medical delivery pens have become widely used in place of, or in addition to, medical syringes, e.g., by diabetics, who frequently inject themselves several times a day with accurately measured, adjustable, pre-selected amounts of insulin or other medication. Medical delivery pens include a reservoir of medication and a distal end adapted to be attached, usually by thread means, to a pen needle assembly. As is well known (see, for example, FIG. 1 of U.S. Pat. No. 5,545,145), a pen needle assembly has, within an outer, generally cylindrical shield, a generally cylindrical housing within which is mounted an axially extending hollow needle, (i) the proximal end of which punctures a seal in the distal end of the medical delivery pen to allow the flow there-through of medication when the delivery pen is screwed into the proximal end of the pen needle cylindrical housing, and (ii) the distal end of which is for insertion into tissue of the person requiring the medication. The pen needle assemblies typically also include a removable thin sterile seal covering the proximal (large diameter) end of the outer shield and a removable tube-like shield covering the distal portion of the hollow needle. The pen needle assembly is then factory sterilized. The user of a pen needle assembly removes the seal from the outer shield, screws the pen into the proximal end of the pen needle housing, removes the outer and tube-like shields, sets the medical delivery pen for the desired dose of medication, and then inserts the distal end of the pen needle into the target tissue following which the medical delivery pen is actuated to deliver the desired dose of medication through the hollow needle into said tissue.

Many diabetics routinely administer medication to themselves several times a day by injection of a pre-selected quantity of insulin (or substitute medication) in liquid form; the correct amount of medication can be determined from prior professional medical instruction or by use of convenient portable blood analysis kits which are small, compact and provide rapid indicators of the user's blood sugar level. Some of the typical several daily injections are often done away from the diabetic's residence which has made the use of the portable, convenient medical delivery pens widespread. The aforesaid testing kits and the medical delivery pens are relatively small in size and can easily fit within a woman's purse or equivalent. A typical scenario for a diabetic at a restaurant for a meal is to first use the blood sugar testing kit to obtain an indicator of his or her blood sugar level. This information then facilitates programming or adjusting the medical delivery pen to deliver the desired quantity of medication. Then the pen with an attached pen needle (a pen needle assembly without the outer cylindrical and tube shields) is used to inject the tissue and dispense the medication. These steps require a relatively short length of time and can be done with minimum loss of privacy. Some people requiring multiple daily medicine injections use both medical syringes and medical delivery pens with pen needles.

Medical delivery pens are also widely used by doctors, nurses and other professionals in their duties. Many individuals will request that an injection be done with a pen needle rather than a syringe. The aforementioned professionals are especially mindful of possible dangers from a needle stick and the possible unwanted "sticks" that occur in the professional world.

The user, both individual and professional, of a pen needle assembly should, after the first use of a pen needle, carefully detach the used pen needle from the medical delivery pen and safely dispose said pen needle into a safe sharps container. The approved disposal procedure is insertion of the distal end of the needle into the tube-like shield (sometimes omitted) and thence the shielded needle and pen needle cylindrical housing into the outer cylindrical shield, unscrewing of the medical delivery pen from the proximal end of the pen needle cylindrical housing, and careful placement of the used pen needle assembly into a safe sharps container. Further, in the "perfect" world, the user of a medical syringe would safely dispose the used syringe into a safe sharps container.

Unfortunately, the recommended safe disposal procedures are not always followed. Used and potentially dangerous syringes, pen needles or pen needle assemblies are routinely left in unsafe places where third parties may unwittingly be "stuck" with possible dire consequences. Examples of such unsafe places are purses, the pockets on the back of aircraft seats, private and public wastebaskets, garbage receptacles, dumpsters and empty milk or other unsafe containers.

Further, the above described pen needle assembly or pen needle disposal procedure requires that the user or associate handle or hold the pen needle while the pen is unscrewed therefrom; this creates the possibility of a potentially dangerous "stick." Also, if the user or associate tries to insert the pen needle into the outer shield to form a pen needle assembly, then additional handling is again required with the possibility of a "stick".

Similar disposal considerations apply to the more traditional syringe needles which may have associated syringe needle covers.

SUMMARY OF THE DISCLOSURE

The present disclosure relates to space efficient systems for distributing, storing, and dispensing a number of medical or laboratory sharps with subsequent safe disposal of the used sharps. Concern about inadvertent transmission of disease through accidental sticks makes it highly desirable to ensure that each used sharps is properly disposed of in an approved sharps container, preferably provided with the sharps at the point of purchase. At the same time, as transportation costs rise, it becomes increasingly desirable to avoid shipping the empty space associated with a sharps disposal container. Each of the embodiments of the system disclosed herein for the efficient distribution and storage of new and used sharps comprises a first container sized to contain and safely dispose of a number of medical or laboratory sharps and a second associated container sized to contain and dispense a similar number of medical or laboratory sharps, wherein the system has a first configuration having a first volume substantially equal to the volume of a first container and a second configuration equal in volume to the sum of the volumes of the first container and a second container having a volume sufficient to contain the number of medical or laboratory sharps.

The system provides an efficient lower volume during shipping and initial storage than would otherwise be obtained when shipping the two containers, yet still provides convenient dispensing of unused sharps and disposal of used sharps in the use location. In a first embodiment, system comprises a first outer container having at least one repositionable wall portion, said repositionable wall portion having a first position and a second position, wherein when the repositionable wall portion is in the first position, the first outer container defines an opening large enough to permit the removal of a quantity of sharps, said sharps selected from pen needles, hypodermic needles, and syringes with attached hypodermic needles, from the first outer container, further wherein when the repositionable wall portion is in the second position, said opening is closed. The first outer container also defines a first aperture which comprises an associated one-way mechanism for conveying a used sharp from the exterior of the first outer container to the interior of the first outer container, wherein said sharp is selected from pen needles, hypodermic needles, and syringes with attached hypodermic needles otherwise known as unibody syringes. The repositionable wall portion and the first outer container cooperatively define a nonreversible locking mechanism for securing said repositionable wall to the first outer container when the repositionable wall is in the second position thereby forming a complete enclosure. The system also comprises a second, inner container sized to fit within the first outer container and to be removed from the first outer container through the opening, wherein said second, inner container contains the quantity of sharps and further comprises a dispensing mechanism for unused sharps.

In a second embodiment, system comprises a first container having at least one repositionable wall portion, said repositionable wall portion having a first position and a second position, wherein when the repositionable wall portion is in the first position, the first container defines an opening large enough to permit the removal of a quantity of sharps, said sharps selected from pen needles, hypodermic needles, and syringes with attached hypodermic needles, from the first container, further wherein when the repositionable wall portion is in the second position, said opening is closed. The first container also defining a first aperture which comprises an associated one-way mechanism for conveying a used sharp from the exterior of the first container to the interior of the first container, wherein said sharp is selected from pen needles, hypodermic needles, and syringes with attached hypodermic needles. The repositionable wall portion and the first container cooperatively define a nonreversible locking mechanism for securing said repositionable wall to the first container when the repositionable wall is in the second position thereby forming a complete enclosure. The system further comprises a second container, having a collapsed distribution configuration and an expanded storage configuration sized to hold the quantity of sharps which are contained within the first container. System embodiments provide a container for the included unused sharps which may be bundled with the sharps disposal container without incurring the penalties associated with shipping, storing, and stocking within the supply chain at least one empty container.

While the invention is amenable to various modifications and alternative forms, specifics thereof have been shown by way of example in the drawings and will be described in detail. It should be understood, however, that the intention is not to limit the invention to the particular embodiments described. On the contrary, the invention is to cover all modifications, equivalents, and alternatives falling within the spirit and scope of the invention.

DETAILED DESCRIPTION OF THE INVENTION

The following description should be read with reference to the drawings wherein like reference numerals indicate like elements throughout the several views. The drawings, which are not necessarily to scale, are not intended to limit the scope of the claimed invention.

All numbers are herein assumed to be modified by the term "about." The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

Although the systems described herein may be readily adapted to distribute and dispense any of a variety of unused sharps and to dispose of them safely after use, it will be convenient to describe certain aspects of the several containers of the system as they relate to specific types of sharp. It will be understood that one of ordinary skill in the art would be capable of modifying the description herein to adapt each of the systems for use with other sharps including, among others, pen needles, pen needle assemblies, hypodermic needles, unibody syringes having integral hypodermic needles, and the like. It will be further understood that the system may be readily adapted to dispense and/or receive more than one type of sharp should that be desired.

Figure 1:
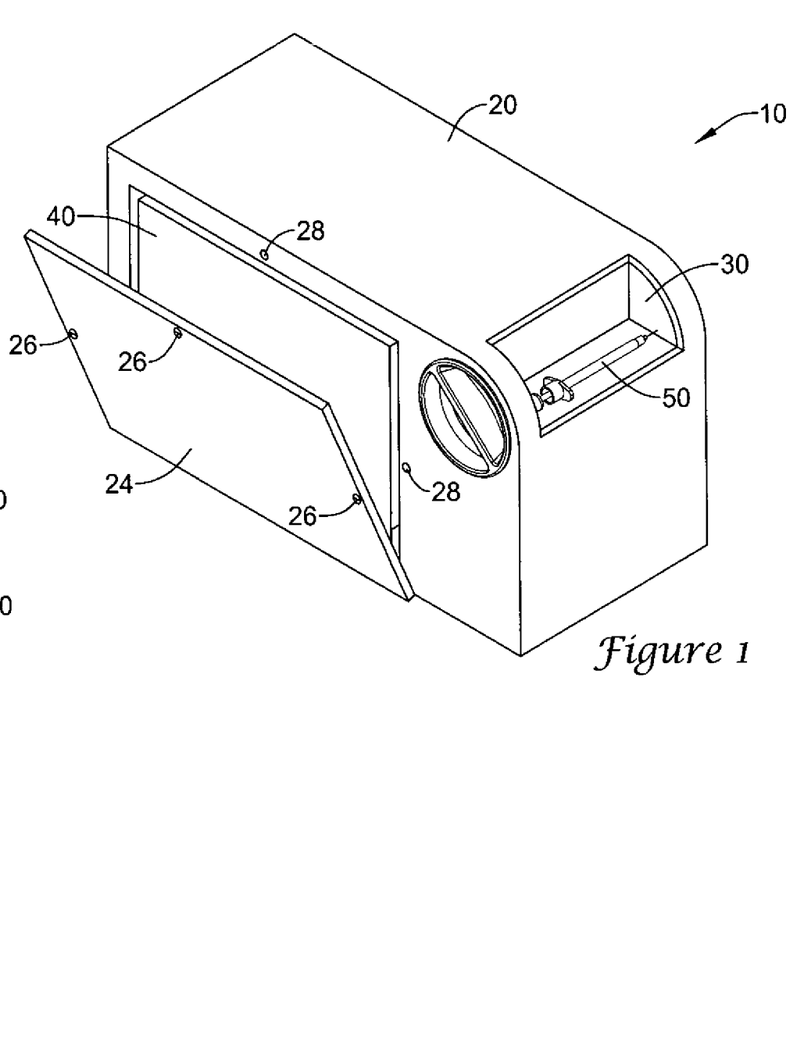
FIG. 1 is a perspective view of an embodiment of the system.
Figure 1A:
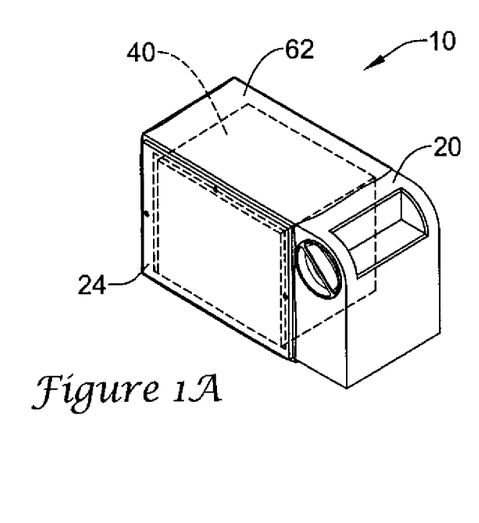
FIG. 1A is a perspective view of the embodiment of FIG. 1.

Referring now to the drawings, FIG. 1 illustrates a system 10 comprising a first outer container 20 having a repositionable wall portion 24. When repositionable wall portion 24 is in a first position, generally associated with shipping and storage, an opening is exposed in container 20, said opening being sufficiently large to allow the removal of an inner container 40 sized to contain a quantity of sharps and to include a dispensing mechanism 22 for unused sharps. The repositionable wall portion 24 and the first outer container 20 cooperatively defining nonreversible locking fasteners 26,28 for securing said repositionable wall portion 24 to the first outer container 20 when the repositionable wall is in the second position thereby forming a complete enclosure. In the illustrated embodiment, the outer container 20 includes an aperture including a rotary mechanism 30 which may convey used syringe 50 into outer container 20. It will be readily appreciated that other mechanisms 30 may be employed for this purpose. FIG. 1 further includes a second inner container 40 sized to contain a quantity of unused sharps, in this embodiment syringes 30, and to include a dispensing mechanism for unused sharps, here represented by dispensing door 22. As illustrated in FIG. 1A, the system 10 may be provided in a shipping configuration in which the opening in container 20 is covered by a shrink wrap material 62. In some embodiments, the shrink wrap material may envelope the repositionable wall portion 24 as well as the first outer container. It will be appreciated that the shrink wrap material may envelope the entire outer container or only that portion necessary to cover the opening in the outer container thereby retaining the inner container 40 during distribution.

Figure 2:
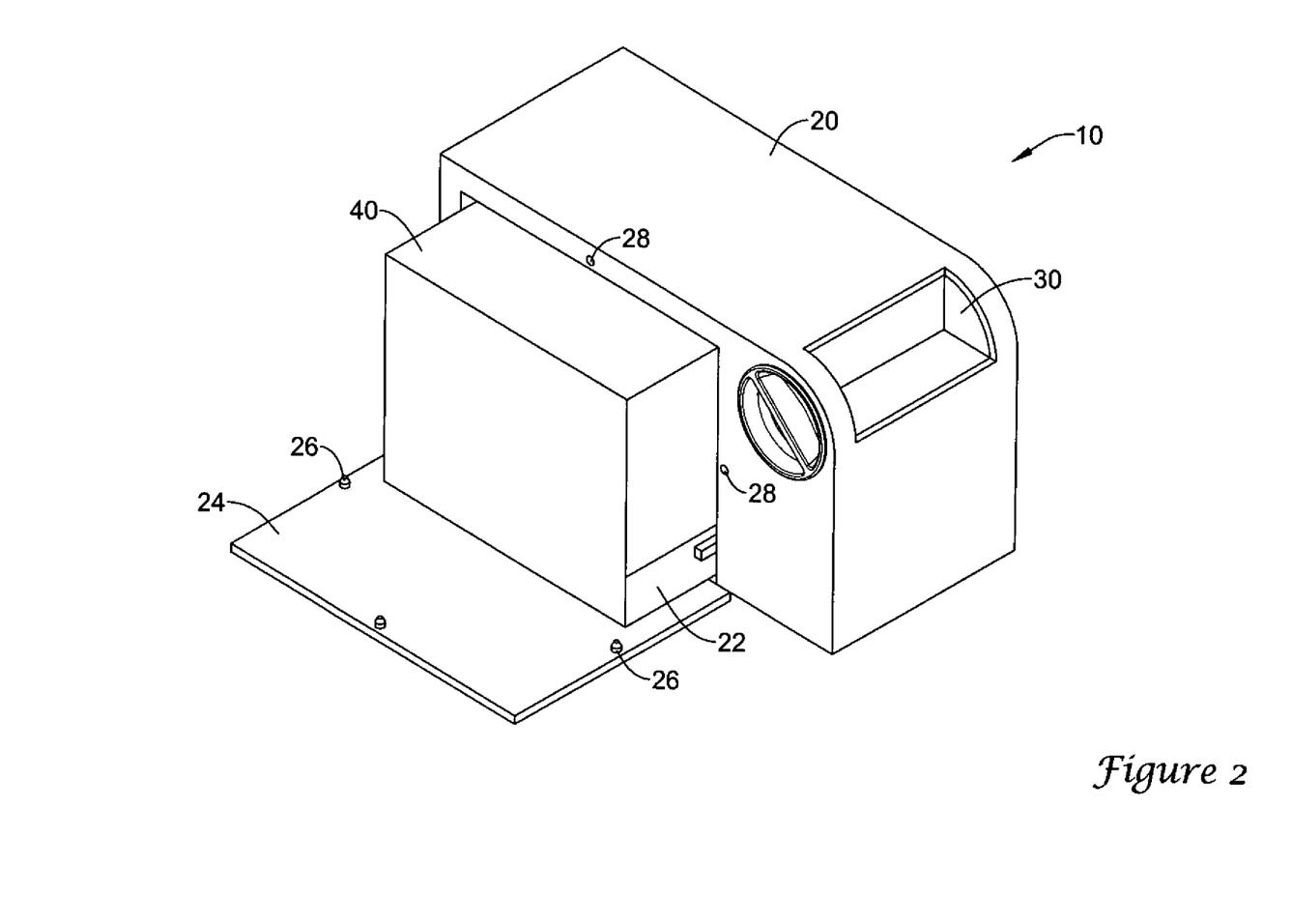
FIG. 2 is a perspective view of the system of FIG. 1 with the second container partially removed.
Figure 3:
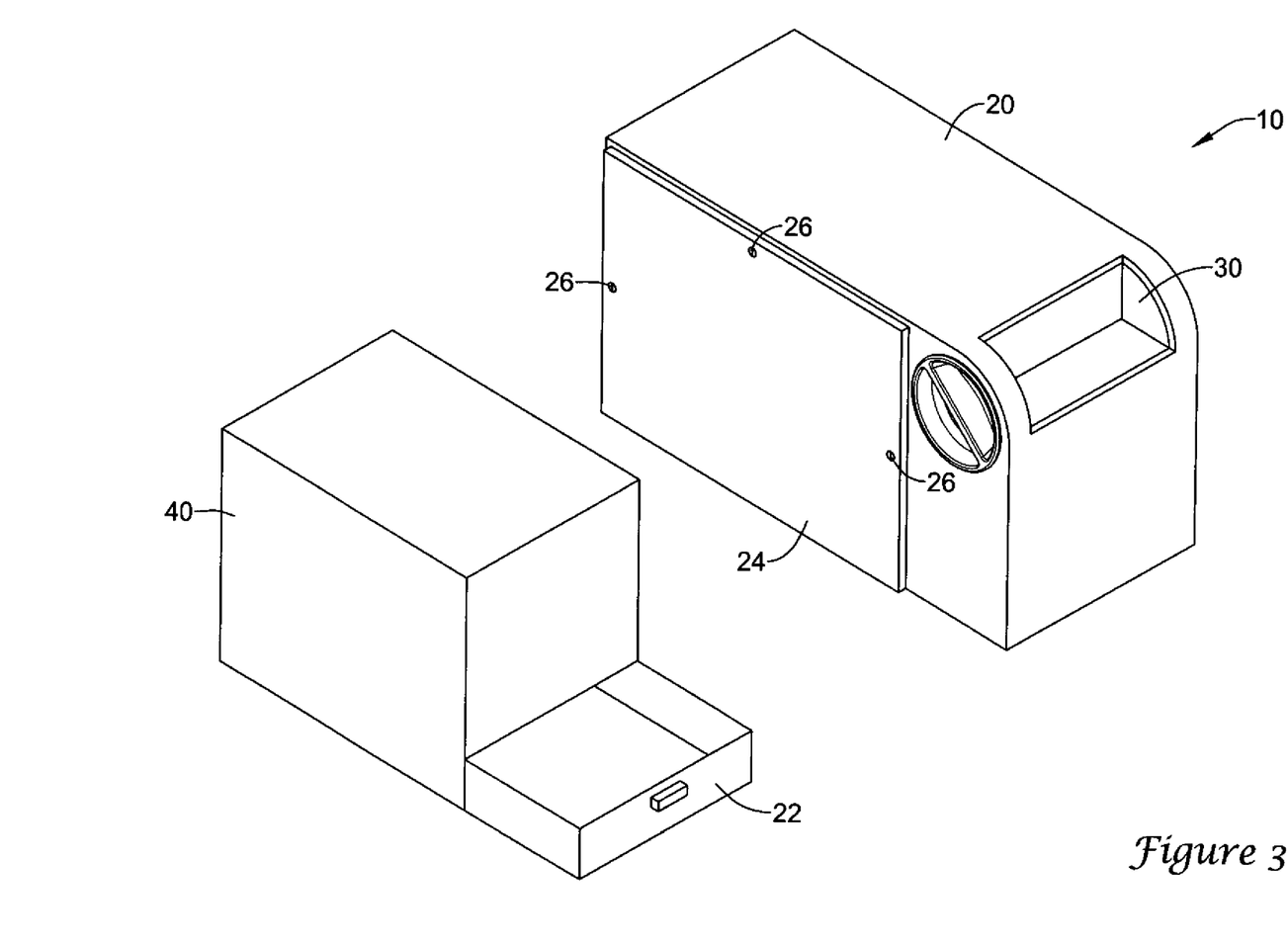
FIG. 3 is a perspective view of the system of FIG. 1 with the second container completely removed.

In FIG. 2, the inner container 40 of system 10 has been partially removed from outer container 20 by sliding over repositionable wall portion 24 which has been pivoted to an open position. It will be appreciated that repositionable wall portion 24 may be completely detached in some embodiments and tethered, hinged, or otherwise pivotably attached to outer container 20 in other embodiments. Continuing to FIG. 3, the system 10 is now configured for use with inner dispensing container 40 completely removed from outer container 20 and with repositionable wall portion 24 in place and locked to outer container 20 by means of nonreversible locking fasteners 26,28. In this configuration of system 10, unused sharps may be removed from inner container 40 through door 22, used, and subsequently returned to the interior of outer container 20 through rotary mechanism 30 for safe disposal.

Figure 4:
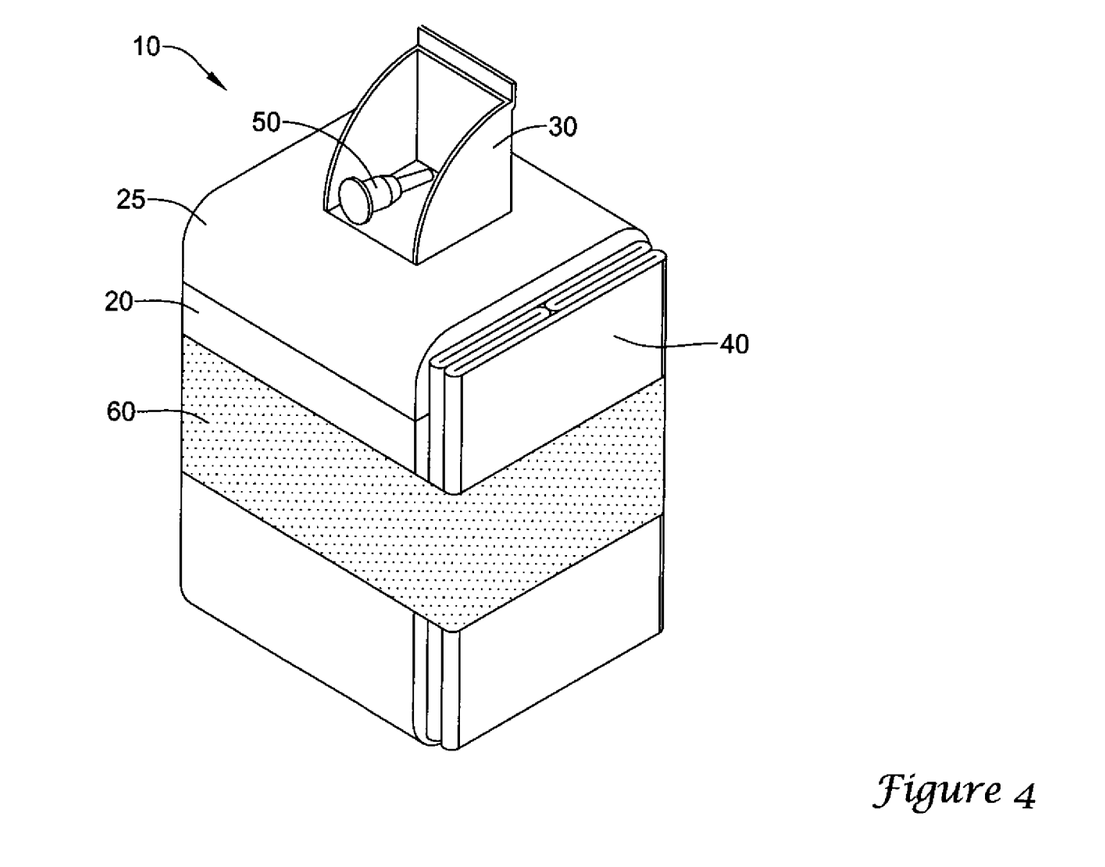
FIG. 4 is a perspective view of an embodiment of the system.

As illustrated in FIG. 4, second container 40 may be supplied as a component of system 10 in the form of a folded container distributed as a component of the system 10. As depicted in FIG. 4, second container 40 is initially secured to the outside of first container 20 by band 60 which holds the components 20,40 of system 10 together during shipping while the unused sharps (not shown) are contained within first container 20. Although second container 40 has been illustrated in the form of an exterior folded container in FIG. 4, it will be readily appreciated that folded container 40 could have been initially stored within first container 20 along with a number of unused sharps. Following distribution of system 10, the user removes removable wall portion 25, including mechanism 30 which will be used to convey used sharp 50, a pen needle assembly in this embodiment, into first container 20, from first container 20 providing access to unused sharps stored therein.

Figure 4A:
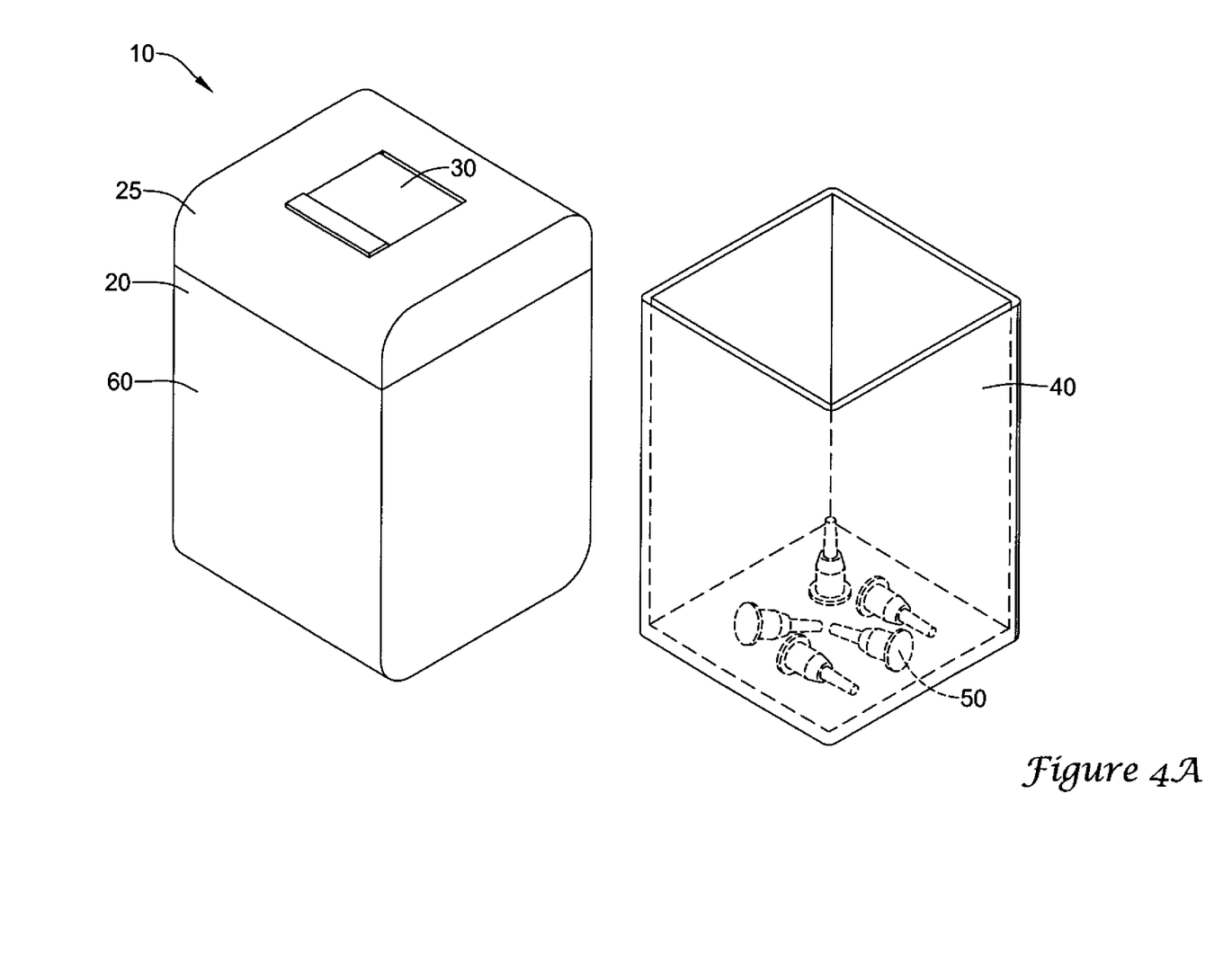
FIG. 4A is a perspective view of the system of FIG. 4 with the second container detached and expanded.

Folded container 40 is then detached from first container 20, or removed from the interior of container 20 in other embodiments, and expanded to provide the unused sharps container 40 of FIG. 4A. The unused sharps 50 are then placed within the expanded container 40 from which they may be dispensed as needed. If desired, an optional dispensing component of container 40 which is not readily collapsed, such as a drawer, may also be removed from the interior of container 20 and installed in container 40 prior to transferring the sharps. Replacement of removable wall portion 25 with engagement of nonreversible locking mechanisms (not shown) completes the deployment of the components of the system 10. In use, unused sharps 50 will be dispensed from expanded container 40, optionally through a dispensing aperture or mechanism analogous to door 22 of FIG. 1. They will subsequently be used and returned to the interior of first container 20 through mechanism 30, here depicted as a pivoting chute. Once the supply of unused sharps has been exhausted, container 40 may again be collapsed for space efficient disposal.

In some embodiments, when the repositionable wall portion is secured to the first outer container by the nonreversible locking mechanism, the complete enclosure is sealed at the perimeter of the repositionable wall portion with respect to liquid leakage from the complete enclosure. In other embodiments, a material capable of absorbing and storing fluid associated with the container is positioned within the first container. In such embodiments, the material capable of absorbing and storing fluid may be selected from organic or inorganic absorbing materials. Any of the known of fluid absorbing materials and forms may be used providing they have sufficient capacity to hold liquids which may incidentally be introduced into the container along with the pen needles, syringe needles, or other sharps to be stored. The following group of absorbing materials is intended to be illustrative and non-limiting. Powders of desiccants such as silica gel, calcium sulfate, calcium chloride, montmorillonite clay, and molecular sieves or organic materials such as polyacrylic acid, polymethacrylic acid, polyacrylamide, and polyalkylene oxide may be provided alone or in layered constructions with a liquid permeable sheet. The polymers may conveniently be provided as nonwoven pads or as powders. In addition to homopolymers such as those listed, the fluid absorbing material may be copolymers and/or optionally may be crosslinked.

The absorbent material may be associated with one or more of the floor and/or walls of the internal storage space. In certain embodiments, the fluid absorbent material within the container has a fluid capacity of at least 0.02 gram for each pen needle, syringe needle or unibody syringe to be stored. In other embodiments, the fluid absorbent material within the container has a fluid capacity of at least 0.05 gram or even at least 0.01 gram for each sharp to be stored. In yet other embodiments, the available fluid capacity per pen needle or syringe needle may be reduced based upon assumptions regarding the rate of evaporation of fluids from the container and the rate at which additional pen needles, syringe needles, or unibody syringes are to be added to the container so long as sufficient capacity is present to absorb the fluid associated with each new sharp deposited.

In some embodiments, when the repositionable wall portion is in the first position, it is pivotably attached to the first outer container along one edge of the repositionable wall portion. In other embodiments, when the repositionable wall portion is in the first position, it is detached from the first outer container. During distribution and storage prior to use, it may be desirable to provide a covering material for the opening in the first container before the repositionable wall portion is secured over the opening following removal of the sharps and second container, if present. In some embodiments, the opening in the outer container is covered by a shrink wrap film. The shrink wrap film may also encompass the repositionable wall portion to create a unitary package for shipping the system. The shrink wrap may also encompass the second container.

In other embodiments, the first container may be contained within a further container which also covers the opening in the first container. In such embodiments, the further container may be, for example, a cardboard box suitable for shipping the system. The further container may also contain the repositionable wall portion and the second container during distribution and storage prior to use. In yet other embodiments, the first container may be contained within the second container during distribution.

In some embodiments, the one-way mechanism which conveys a used sharp into the first container may be functional in two or more orientations of the first container. That is, the one-way mechanism may be accessible and functional in two or more orientations of the first container which differ in that the container rests on different faces in the two orientations. For example, in a first orientation, the container may rest upon a small face such that its greatest dimension is substantially vertical, while in the second orientation the greatest dimension may be substantially horizontal. It will be understood that some containers may be substantially equal in all dimensions and still have orientations which differ with respect to which face of the container forms the base and also with respect to the orientation of the aperture associated with one-way mechanism. In some embodiments, the one-way mechanism is configured to accept and facilitate the removal of a hypodermic needle from one of an associated syringe and an injection pen. In some of those embodiments the removed hypodermic needle may be conveyed directly into the second compartment following removal. The one-way mechanism may have any of the configurations known in the art at the time that the device is designed. For example, the one-way mechanism may be a rotating mechanism, a pivoting mechanism, a sliding mechanism, or a largely passive flexing mechanism such as a diaphragm.

In some embodiments, the portion of the first container which receives sharps such as pen needles, pen needle assemblies, syringe needles, syringe needle covers, and combinations thereof provides a visual contrast to the surrounding portions of the housing to aid visually impaired users in properly orienting and inserting the pen needles, pen needle assemblies, syringe needles, syringe needle covers, and combinations thereof. The visual distinctive feature may be provided in the form of color contrast and/or patterning relative to the surrounding housing. Preferably, the color associated with the receiving region or a patterned portion thereof will be red. In some embodiments, the means for receiving pen needles includes a combination of protrusions and recesses which engage the pen needle to prevent rotation thereof as a pen is rotated relative to the pen needle within the said means. This engagement facilitates one hand removal of a pen needle from a medical delivery pen, thereby minimizing the risk of accidental sticks.

In some embodiments, the means for receiving pen needles, pen needle assemblies, syringe needles, syringe needle covers, and combinations thereof includes a means for rotating the receiving means relative to the housing. In certain embodiments, the rotation will be about an axis generally perpendicular to an axis associated with the pen needle, pen needle assembly, syringe needle, syringe needle cover, or combinations thereof which are to be conveyed into the interior storage space. In other embodiments, the rotation will be about an axis which is generally parallel to an axis associated with the pen needle, pen needle assembly, syringe needle, syringe needle cover, or combinations thereof which are to be conveyed into the interior storage space. The means for rotating the receiving means may be either manual or automated as by a spring drive or electric motor.

In some embodiments, the means for receiving pen needles, pen needle assemblies, syringe needles, syringe needle covers, and combinations thereof includes an ejector assembly having an ejector axis and wherein the means for receiving pen needles, pen needle assemblies, syringe needles, syringe needle covers, and combinations thereof is operatively coupled to the means for rotating said receiving means relative to the housing. In those embodiments, rotation of the receiving means may convey the pen needles, pen needle assemblies, syringe needles, syringe needle covers, and combinations thereof within the internal storage space whereupon the ejector assembly ejects the pen needle, pen needle assembly, syringe needle, syringe needle cover, or combinations thereof from the receiving means into the internal storage space.

In some embodiments, the container includes one or more guards which prevent pen needles, pen needle assemblies, syringe needles, syringe needle covers, or combinations thereof within the internal storage space from re-entering the means for receiving and ejecting pen needles, pen needle assemblies, syringe needles, syringe needle covers, and combinations thereof. This is desirable to prevent accidental or intentional removal of sharps from the internal storage space, particularly when the container is inverted or otherwise placed in an orientation other than that normally employed for disposing of sharps. Absent such guards, sharps might accidentally be released during transport. In certain embodiments, the one or more guards are structures within the internal storage space which prevent access to the receiving means in positions other than those associated with receiving or ejecting pen needles, pen needle assemblies, and combinations thereof.

In those embodiments in which the second container includes a dispensing mechanism, the mechanism may be configured to facilitate removal of a single unused sharp or it may be configured to facilitate removal of multiple sharps. For example, the sharps may be removed in individual containers such as pen needle assemblies, covered hypodermic needles, covered unibody syringes, or the like. Alternatively, the sharps may be removed as prepackaged multiple sharps, for example, a package of two pen needle assemblies. In some embodiments, the sharps may be presented at the aperture in the form of a continuous strip of packaged sharps from which the user may selectably remove one or more sharps as desired. The mechanisms may include doors, drawers, and the like. In other embodiments, the unused sharps may be associated with a roll, reel, stack, serpentine ribbon, or the like which may convey the sharps sequentially to the dispensing mechanism.

Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

What is claimed is:

1. A system for the efficient distribution and storage of new and used sharps, the system comprising:
    a first outer container having at least one repositionable wall portion, said repositionable wall portion having a first position and a second position, wherein when the repositionable wall portion is in the first position, the first outer container defines an opening large enough to permit the removal of a quantity of sharps, said sharps selected from pen needles, hypodermic needles, and syringes with attached hypodermic needles, from the first outer container, further wherein when the repositionable wall portion is in the second position, said opening is closed;

the first outer container also defining a first aperture which comprises an associated one-way mechanism for conveying a used sharp from the exterior of the first outer container to the interior of the first outer container;

the repositionable wall portion and the first outer container cooperatively defining a nonreversible locking mechanism for securing said repositionable wall to the first outer container when the repositionable wall is in the second position thereby forming a complete enclosure and thereby prohibiting any sharps from exiting the complete enclosure; and a second, inner container sized to fit within the first outer container and to be removed from the first outer container through the opening therein, wherein said second, inner container when removed contains the quantity of sharps and further comprises a dispensing mechanism for unused sharps, wherein the second inner container when full of unused sharps contains the quantity of sharps, which sharps can be contained within the first container.

2. The system of claim 1, wherein when the repositionable wall portion is secured to the first outer container by the nonreversible locking mechanism, the complete enclosure is sealed at the perimeter of the repositionable wall portion with respect to liquid leakage from the complete enclosure.

3. The system of claim 1, wherein when the repositionable wall portion is in the first position, it is pivotably attached to the first outer container along one edge of the repositionable wall portion.

4. The system of claim 1, wherein when the repositionable wall portion is in the first position, it is detached from the first outer container.

5. The system of claim 1, wherein when the second inner container is within the first outer container and the repositionable wall portion is in the first position, the opening in the first outer container is covered.

6. The system of claim 5, wherein the opening in the first outer container is covered by a further container which envelopes the first outer container.

7. The system of claim 6, wherein the further container which envelopes the first outer container also envelopes the repositionable wall portion.

8. The system of claim 1, wherein said first outer container further comprises a liquid absorbent material having a liquid capacity of at least 0.002 gram per contained sharp.

9. The system of claim 1, wherein said first outer container further comprises a liquid absorbent material having a liquid capacity of at least 0.01 gram per contained sharp.

10. The system of claim 1, wherein the one-way mechanism associated with the first aperture is functional in two or more orientations of the first outer container.

11. The system of claim 1, wherein the one-way mechanism associated with the first aperture is configured to accept and facilitate the removal of a hypodermic needle from one of an associated syringe and an injection pen, further wherein the removed hypodermic needle is conveyed directly into a second compartment.

12. The multifunctional container of claim 1, wherein the one-way mechanism associated with the first aperture is a rotating mechanism.

13. The multifunctional container of claim 1, wherein the one-way mechanism associated with the first aperture is a pivoting mechanism.

14. The multifunctional container of claim 1, wherein the one-way mechanism associated with the first aperture includes a sliding component.

* * * * *